(12) United States Patent
Bond et al.

(10) Patent No.: US 9,187,399 B2
(45) Date of Patent: Nov. 17, 2015

(54) PRODUCTION OF MALEIC OR FUMARIC ACID FROM LEVULINIC ACID

(71) Applicants: Jesse Quentin Bond, Syracuse, NY (US); Anargyros Chatzidimitriou, Syracuse, NY (US)

(72) Inventors: Jesse Quentin Bond, Syracuse, NY (US); Anargyros Chatzidimitriou, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 14/592,435

(22) Filed: Jan. 8, 2015

(65) Prior Publication Data

US 2015/0191411 A1    Jul. 9, 2015

Related U.S. Application Data

(60) Provisional application No. 61/924,736, filed on Jan. 8, 2014.

(51) Int. Cl.
*C07C 51/367* (2006.01)
*B01J 8/02* (2006.01)

(52) U.S. Cl.
CPC ............. *C07C 51/367* (2013.01); *B01J 8/0285* (2013.01); *B01J 2208/027* (2013.01)

(58) Field of Classification Search
CPC .. C07C 51/367; B01J 8/0285; B01J 2208/027
See application file for complete search history.

(56) References Cited

U.S. PATENT DOCUMENTS 2,676,186 A    4/1954   Dunlop
8,389,761 B2 *  3/2013   Dumesic et al. .............. 562/577

FOREIGN PATENT DOCUMENTS

WO    2012044168    4/2012

* cited by examiner

*Primary Examiner* — Shailendra Kumar
(74) *Attorney, Agent, or Firm* — David L. Nocilly; George R. McGuire; Bond Schoeneck & King, PLLC

(57) ABSTRACT

The production of maleic acid and fumaric acid (or the anhydride form of either, maleic anhydride) via gas-phase, oxidative cleavage of levulinic acid in a single packed bed reactor over a reducible oxide catalyst. The production may be carried out in an initial mixing vessel into which levulinic acid is continuously charged and mixed with both inert (He, $N_2$, Ar, etc.) and oxidizing ($O_2$, air, etc.) gases. The feed stream can then be safely heated to reaction temperature, which generally ranges from 200-500° C., without initiating polymerization, in a second stage preheater that thermally equilibrates the gaseous mixture of LA, O2, and inert diluent and fed to a third stage catalytic reactor for final processing.

9 Claims, 5 Drawing Sheets

PRODUCTION OF MALEIC OR FUMARIC ACID FROM LEVULINIC ACID

CROSS-REFERENCE TO RELATED APPLICATIONS

The present application claims priority to U.S. Provisional Application No. 61/924,736, filed on Jan. 8, 2014.

BACKGROUND OF THE INVENTION

1. Field of the Invention

The present invention relates to the production of maleic acid, its isomer fumaric acid, the anhydride of either maleic or fumaric acid (maleic anhydride) and, more particularly, the oxidation of levulinic acid to yield maleic acid, fumaric acid, or maleic anhydride.

2. Description of the Related Art

Concern over diminishing fossil reserves has increased interest in the production of industrial commodities (transportation fuels, commodity chemicals, etc.) from biomass resources. In particular, lignocellulosics (e.g., woody biomass) are viewed as an ideal alternative source of industrial carbon (i.e., alternative to petroleum) since they are abundant, easily cultivated, often grow on marginal land, and require minimal resource inputs compared to conventional food crops.

Despite the interest in establishing lignocellulosic biorefineries on a large scale, no technologies have to date proven cost effective. The source of the lack of economic viability despite a myriad of potential options for biomass processing is complex; however, it can be generally summarized as a tension between the ease of converting biomass to a potentially useful industrial commodity and the revenue that can be generated from said product. In general, transportation fuels are a difficult market to enter as lignocellulosic fuels must compete with relatively low cost petroleum and a well-optimized refinery structure built around the large scale production of transportation fuels. Despite large markets in the transportation sector, biofuels—particularly lignocellulosic biofuels—have been unable to compete with conventional fuels. Further, they are unlikely to be competitive with petroleum-based fuels for the foreseeable future. Even inexpensive lignocellulosic commodities, such as pyrolysis oils, require extensive upgrading before their properties match those of the hydrocarbon fuels required in the current infrastructure. As such, lignocellulosic fuels will likely remain prohibitively expensive in the near term. In contrast, chemical products are relatively difficult to derive from petroleum and generally offer higher profit margins. Further, chemical targets are often more straightforward to produce from biomass than via competing peteroleum based strategies. This suggests that lignocellulosic chemical products could be economically viable in the near term, allowing a portion of the peterochemicals industry to shift toward using renewable feedstocks.

Levulinic acid, as seen in FIG. 1, is one such example of an attractive chemical product that is relatively easy to source from lignocellulose. The entire carbohydrate content of lignocellulose (i.e., hemicellulose, cellulose, and sugars derived therefrom) can be converted into levulinic acid using well established technologies. For example, the BioFine Process has been optimized to produce Levulinic acid from six-carbon sugars such as the glucose subunits forming cellulose in yields as high as 75% of the theoretical maximum. If five-carbon sugars are present in biomass, they are converted to furfural by acid hydrolysis and can be recovered as co-products of LA production. Furfural is presently produced at commodity scales by acid hydrolysis of xylan rich corn waste (e.g., cobs). Once formed, furfural can be converted to levulinic acid in high yields by sequential hydrogenation (to form furfuryl alcohol) and hydrolysis (to form levulinic acid). Given that C5 and C6 sugars generally comprise up to 80 wt % of lignocellulose, LA appears to be an attractive chemical intermediate that is relatively easy to produce from sugars and can utilize a large fraction of the available feedstock.

Presently, LA is a relatively expensive chemical intermediate, and no existing industry relies on this molecule as a precursor; as such, despite its straightforward production, there are presently no large scale off-takers for LA, and development of the industry has largely stalled despite its promise. This has motivated research to identify strategies by which LA can be easily converted into a target product that does have a robust market. Much of the effort has pursued efficient production of transportation fuels from LA; however, no matter how efficient the upgrading, LA-based fuels are not yet competitive with petroleum derived alternatives.

BRIEF SUMMARY OF THE INVENTION

The present invention comprises an alternative approach for LA upgrading which targets an existing commodity chemical market that could provide sufficiently large profit margins to enable an economically viable LA-based biorefinery. In particular, the present invention involves the production of maleic acid, its isomer fumaric acid, or the anhydride form of either, maleic anhydride, via gas-phase, oxidative cleavage of levulinic acid (or angelicalactones, which form reversibly from levulinic acid under reaction conditions) in a single packed bed reactor over a reducible oxide catalyst. The present invention further involves an apparatus designed specifically to carry out the transformation. In particular, the apparatus is comprised of an initial mixing vessel into which levulinic acid is continuously charged and mixed with either or both inert (He, $N_2$, Ar, etc.) and oxidizing ($O_2$, air, etc.) gases. With the LA diluted into a gas stream with a relatively high linear velocity in process tubing, the feed stream can then be safely heated to reaction temperature, which generally ranges from 200-500° C., without initiating polymerization. This can be accomplished in a second stage preheater that immediately precedes the catalytic reactor to allow thermal equilibration of the gaseous mixture of LA, $O_2$, and inert diluent at the reactor temperature prior to introduction into a catalytic reactor, or in a single reaction vessel used for the first stage.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 6:
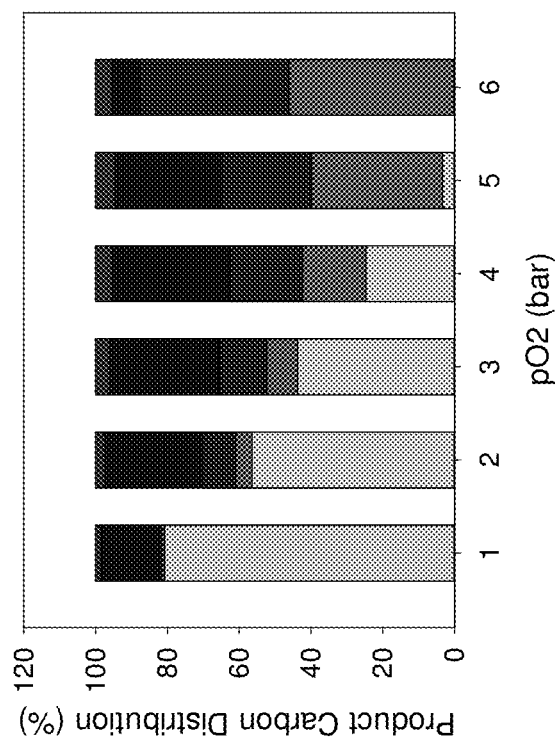
Figure 6:
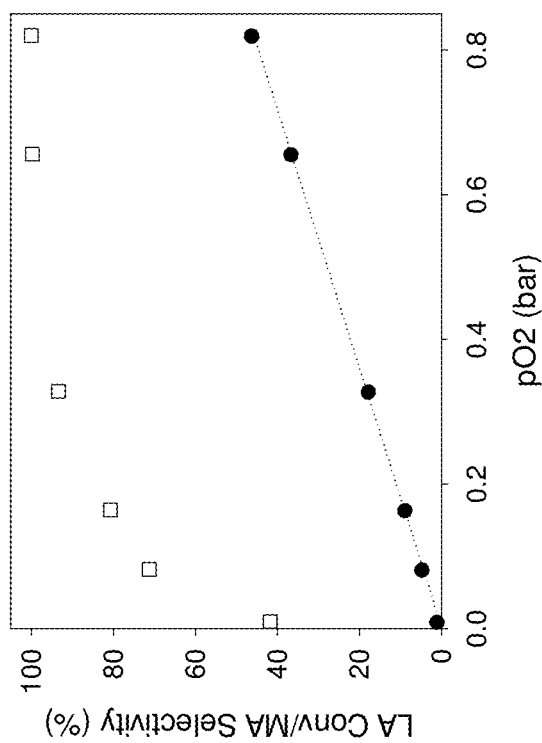

angelicalactones, (gray fill) maleic acid, (dark gray fill) Cox, (Pattern fill) diones, (Black fill) other, e.g., acetic acid, acetaldehyde, and propionaldehyde;

FIG. 6 is a series of graphs showing the influence of Oxygen partial pressure on LA conversion, MA selectivity and the Influence of $O_2$ partial pressure on product carbon distribution, with the following products represented from the axis upward: angelicalactones, MA, COx, diones, other.

DETAILED DESCRIPTION OF THE INVENTION

Figure 1:
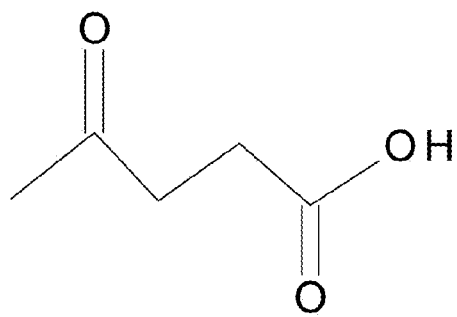
FIG. 1 is a schematic of the structure of levulinic acid.
Figure 2:
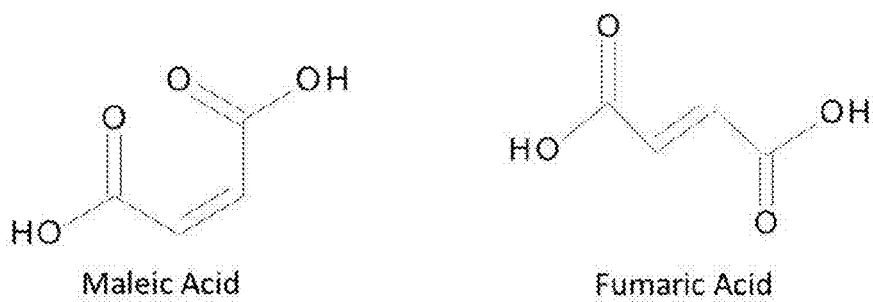
FIG. 2 are schematics of the structures of maleic acid and fumaric acid.

Referring now to the drawings, wherein like reference numerals refer to like parts throughout, the present invention is the production of maleic acid and its isomer fumaric acid, as seen in FIG. 2 (or the anhydride form of either, maleic anhydride) via gas-phase, oxidative cleavage of levulinic acid (or angelicalactones, which form reversibly from levulinic acid under reaction conditions) in a single packed bed reactor over a reducible oxide catalyst. Stereoisomers maleic and fumaric acid could supply the existing maleic anhydride market, which is substantial and offers a higher selling price than conventional fuels. As such, from the standpoint of attracting investment in lignocellulo sic technologies, a simple strategy for production of maleic (or fumaric) acids—such as the one proposed here from levulinic acid—could have a substantial impact.

The present invention comprises both a method of performing chemical transformation wherein levulinic acid undergoes oxidative cleavage, dehydration, and/or dehydrogenation reactions to form maleic acid, fumaric acid, or maleic anhydride, and an apparatus designed specifically to carry out the transformation. Since the reaction occurs in the gas phase and levulinic acid is both reactive and nonvolatile, a system for levulinic acid vaporization is non-trivial and additionally disclosed herein.

Figure 3:
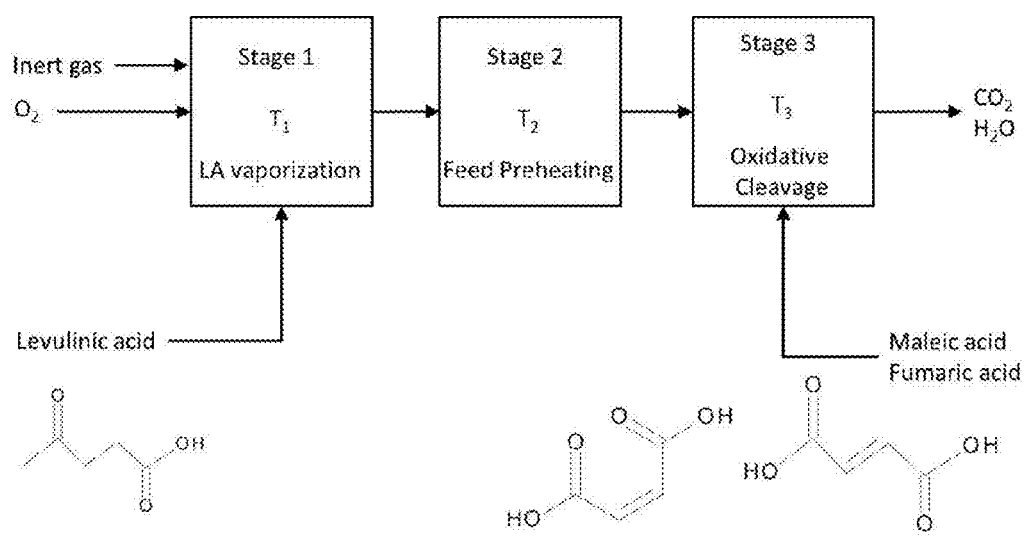
FIG. 3 is a schematic of the production of maleic and fumaric acids from levulinic acid.

There is seen in FIG. 3 an illustration of the process of forming maleic acid. The present invention could be easily implemented by emerging levulinic acid producers as a modular add-on to transform their current product (for which no real commercial markets exist) into a value added commodity chemical that is globally important in the production of polymers and solvents. For the purposes of the present invention, references to maleic acid generally include, unless otherwise specified maleic acid, the isomer fumaric acid, or maleic anhydride.

The apparatus of the present invention comprises an initial mixing vessel into which levulinic acid is continuously charged and mixed with either or both inert (He, $N_2$, Ar, etc.) and oxidizing ($O_2$, air, etc.) gases. The temperature and pressure of the vessel are independently controlled alongside gas and levulinic acid flow rates to permit a range of vapor-phase LA concentrations (e.g., 0-1 bar) and molar LA feed rates. In a preliminary analysis, liquid LA will gradually polymerize at temperatures required for vaporization, fouling the reaction vessel. Polymer formation can be mitigated by reducing the length of time for which LA is retained at elevated temperatures, and the apparatus described here achieves this by delivering a continuous feed of LA to a saturation chamber wherein the feed rate of LA is adjusted such that the LA partial pressure is below its vapor pressure at the temperature maintained in the mixing vessel. A preferred method is to fix the temperature of the mixing vessel at or below 150° C.; however, higher temperatures—in theory governed only by the operating limits of the mixing vessel—may be employed to achieve higher gas-phase concentrations of levulinic acid. In general, low temperatures are preferred in the mixing vessel because polymerization of the LA occurs slowly, allowing for the LA to be vaporized and diluted with inert gas to a point at which its concentration is sufficiently low to prevent degradation upon heating. With the LA diluted into a gas stream with a relatively high linear velocity in process tubing, the feed stream can then be safely heated to reaction temperature, which generally ranges from 150-500° C. The preferred approach is to heat the gas feed to reaction temperature in a second stage preheater that immediately precedes the catalytic reactor; however, this is optional and not integral to the design of the process as all heating can occur in a single vessel. Finally, the gaseous mixture of LA, $O_2$, and (optional) inert diluent are exposed to the catalytic reactor. In this example, we have employed a packed bed, though any type of catalytic reactor (e.g., batch, fluidized bed, recirculating, spinning basket, etc.) could alternatively be used. The catalytic reactor in this case is comprised of a tube or set of tubes optionally filled with a mixture of inert diluent material (alumina, quartz, etc.) and a second catalytic material which is generally a reducible oxide (Vanadia, Ceria, Titania, etc.) but could ostensibly be any solid material having both redox and/or acid functionality. If an oxide is used, it may be a bulk oxide. If desired, a reactive oxide with low surface area may be supported on a second, high surface area material to improve dispersion. Examples of appropriate supports include but are not limited to amorphous SiO2, Al2O3, TiO2, ZrO2, C, hexagonal mesoporous silicas, zeolites, amorphous silica aluminas, SAPOs, etc. In general, any conventional catalysts support is applicable for this system. In the preferred version of the invention, $V_2O_5$ was supported on γ-alumina or amorphous $SiO_2$, and the preparation for this material is summarized below. For the purposes of illustration, the preparation for a supported $V_2O_5$ is listed here; however, this procedure is well established and not claimed as part of the current invention. It may be generalized to accommodate $V_2O_5$ on a variety of supports. Other reducible oxides or redox active materials prepared analogously from cerium, zirconium, titanium, molybdenum, tungsten, etc. could be similarly applicable for this process.

Catalysts were prepared by incipient wetness impregnation of ammonium metavanadate dissolved in aqueous, 1 M oxalic acid onto the desired support (e.g., γ-alumina, $SiO_2$, $TiO_2$, etc.). The catalyst was crushed and sieved to achieve uniform particle size and finally was activated by holding the sample under flowing air for 4 hours at 500° C. This comprises a generic calcination procedure for solid oxides, and any range of temperatures, contact times, and oxidizing gas blends could alternatively be employed.

All reaction experiments were run in the gas phase, in a ½" downflow stainless steel tubular reactor. A desired mass of catalyst (e.g., $V_2O_5$ on $Al_2O_3$) was held halfway through the length of the tube between two pieces of quartz wool, while the remainder of the tube was filled with quartz chips to ensure uniform mixing and minimize the dead volume of the reactor. A 12" long ceramic furnace (Omega) was used to heat the reactor. Prior to each experiment, the catalytic reactor was calcined at 500° C. to ensure that it was free of any water or carbonaceous species.

A preheated mixing section was held at a temperature of 150° C., and separate Feeds of LA (controlled by syringe pump), $O_2$ (controlled by mass flow controller) and $N_2$ (controlled by mass flow controller) were first preheated to 150° C. and introduced to the mixing stage. The LA and gas feed rates were maintained for the duration of operation such that the LA was fully vaporized in the initial mixing stage, and its partial pressure was held below its vapor pressure (0.026 atm at 150° C.) at all of the process sections between the vaporizing section and the reactor exit. This prevented LA condensation, which leads to polymerization and reactor fouling. The gaseous mixture was subsequently heated to reaction temperature in a second preheating stage and finally introduced into the reactor. All temperatures were monitored with K-type thermocouples and controlled using temperature controllers. Many possible combinations of T, LA, O2, and N2 molar feed rates can be employed depending on the scale of the reactor and the desired concentration of LA so long as the partial pressure of LA is retained below the vapor pressure of LA at a given operating condition.

At the exit of the catalytic reactor, liquid and gaseous products were separated using a condenser, which was typically immersed in a cryogenic bath to allow rapid condensation of LA and reaction products, such as maleic, fumaric, and succinic acid, which are not well-suited to gas chromatography. Condensable species recovered from the reaction system included levulinic acid, alpha- and beta-angelicalactones, cyclopentanedione, methylvinylketone, acetic acid, propionic acid, maleic acid, succinic acid, maleic anhydride, and succinic anhydride. Formation of fumaric acid is assumed to occur alongside that of maleic acid since the two are cis/trans isomers, and either can form maleic anhydride, which is observed as a reaction product. With the exception of the diacids (maleic, fumaric, succinic) and acid anhydrides (maleic and succinic), all species were quantitatively analyzed by an Agilent 7890 GC equipped with an FID detector and an HP-INNOWAX column. Qualitative product identification was achieved using an Agilent 7890 GC-MS equipped with an Agilent 5975C detector and an HP-INNOWAX column. Maleic acid, fumaric acid, succinic acid, succinic anhydride, and maleic anhydride were quantified in an Agilent series 1100 HPLC equipped with a Zorbax Eclipse Plus C18 column and a Zorbax Sb-Aqueous column connected in series or an Agilent Hi-Plex column. All quantitative analysis on the HPLC was performed using a UV detector.

Gaseous products were passed through an on-line Agilent 7890 GC equipped with two injectors, two columns, and two detectors. The first is an HP-5 column connected to an FID detector, for the quantification of hydrocarbons and the second is a Restek Shincarbon column connected to a TCD detector, for the quantification of CO and $CO_2$.

Using the above described apparatus, the data summarized in Table 1 was collected, which summarizes key data generated during the oxidative cleavage of LA over bulk and supported $V_2O_5$. Each supported catalyst employed herein was prepared at a 7 VOx sites $nm^{-2}$ of support surface area. Table 1 provides a summary of preliminary results for oxidation of LA and 2-pentanone over various $V_2O_5$ systems, where the conditions were 0.035 bar, 0.35 bar $O_2$, 0.65 bar He, with space velocity is defined as moles of organic per mole of Vanadium per minute.

TABLE 1

| Entry | Catalyst | Feed | Space Velocity ($min^{-1}$) | T (K.) | Conversion | Selectivity $C_4$ | $C_2$ | Other |
|---|---|---|---|---|---|---|---|---|
| 1 | $V_2O_5$ | LA | 0.7 | 648 K. | 90% | 12% | 15% | 73% |
| 2 | $V_2O_5$/$SiO_2$ | LA | 0.6 | 648 K. | 95% | 30% | 8% | 62% |
| 3 | $V_2O_5$/$TiO_2$ | LA | 21 | 648 K. | 99% | 0.3% | 2% | 98% |
| 4 | $V_2O_5$/$Al_2O_3$ | LA | 1 | 648 K. | 94% | 33% | 3% | 64% |
| 5 | $V_2O_5$/$Al_2O_3$ | LA | 1 | 623 K. | 76% | 46% | 4% | 50% |

Over bulk $V_2O_5$ (Entry 1), 90% conversion of LA was observed and selectivities of 12% and 15% toward terminal and internal bond cleavage, respectively. Entry 2 summarizes results for $V_2O_5$/$SiO_2$. For $V_2O_5$/$SiO_2$, 30% and 8% selectivities to $C_4$ diacids and C2 products was observed, respectively. $V_2O_5$/$TiO_2$ (entry 3) is substantially more active than either bulk $V_2O_5$ or $V_2O_5$/$SiO_2$, and complete LA conversions were observed even upon an order-of-magnitude increase in space velocity; however, $V_2O_5$/$TiO_2$ displays poor selectivity for terminal C—C cleavage. Over $V_2O_5$/$TiO_2$, decarbonylation to form methylvinylketone was predominantly observed. $V_2O_5$/$Al_2O_3$ was employed subsequently (entries 4 and 5) and offers relatively high selectivity at 648° K to terminal C—C cleavage (33%) compared to internal cleavage (3%). Selectivity to C4 diacids can be improved by decreasing the temperature to 623° K, where a selectivity of 46% to $C_4$ diacids at an LA conversion of 76% was observed, corresponding to a yield of 36%.

Figure 4:
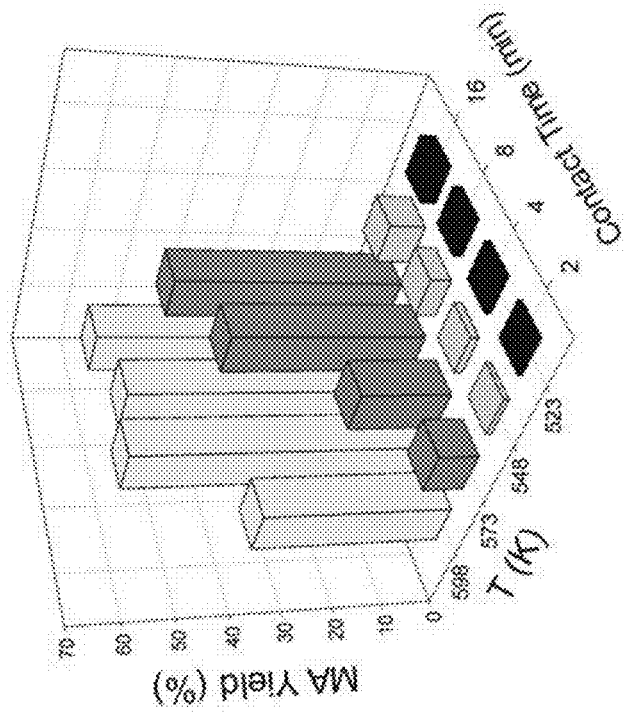
FIG. 4 is a series of graphs showing levulinic acid conversion and Maleic Acid yields obtained from 523 K to 598 K as a function of contact time and a percentage of theoretical maximum.
Figure 4:
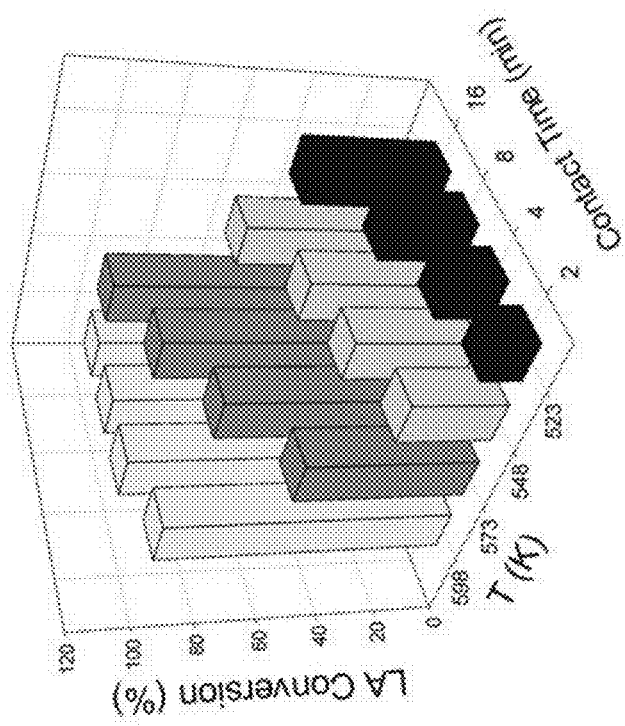

Referring to FIG. 4, LA conversion and Maleic acid yields were attained over VOx/$Al_2O_3$ through a range of temperatures and contact times. Levulinic acid conversion and maleic acid yields were obtained from 523° K to 598° K as a function of contact time. Here, MA yield is defined as a percentage of theoretical maximum. Contact times are calculated as the molar loading of vanadium in a given reactor normalized by the molar feed rate of LA into the reactor. For each experiment shown, LA was introduced at a partial pressure of 0.0158 bar, the O2 partial pressure was 0.33 bar. As seen in FIG. 4, LA conversion increases with both temperature and contact time, and MA yields generally follow the same trend. At temperatures of 573° K and above, LA conversion generally approaches 100%, and at 598° K and above, LA is completely consumed over the entire range of contact times. From high temperature data at 598 and 623° K, it is apparent that MA yields increase with contact time despite invariant LA conversion, indicating that selectivity to MA relative to competing products is generally enhanced at higher temperatures and longer contact times. This suggests multiple side reactions compete with oxidative cleavage. Over VOx/$Al_2O_3$ in the reported range of experimental conditions, the highest MA yields observed were between 55 and 60% at 598° K and contact times between 4 and 16 min.

Figure 5:
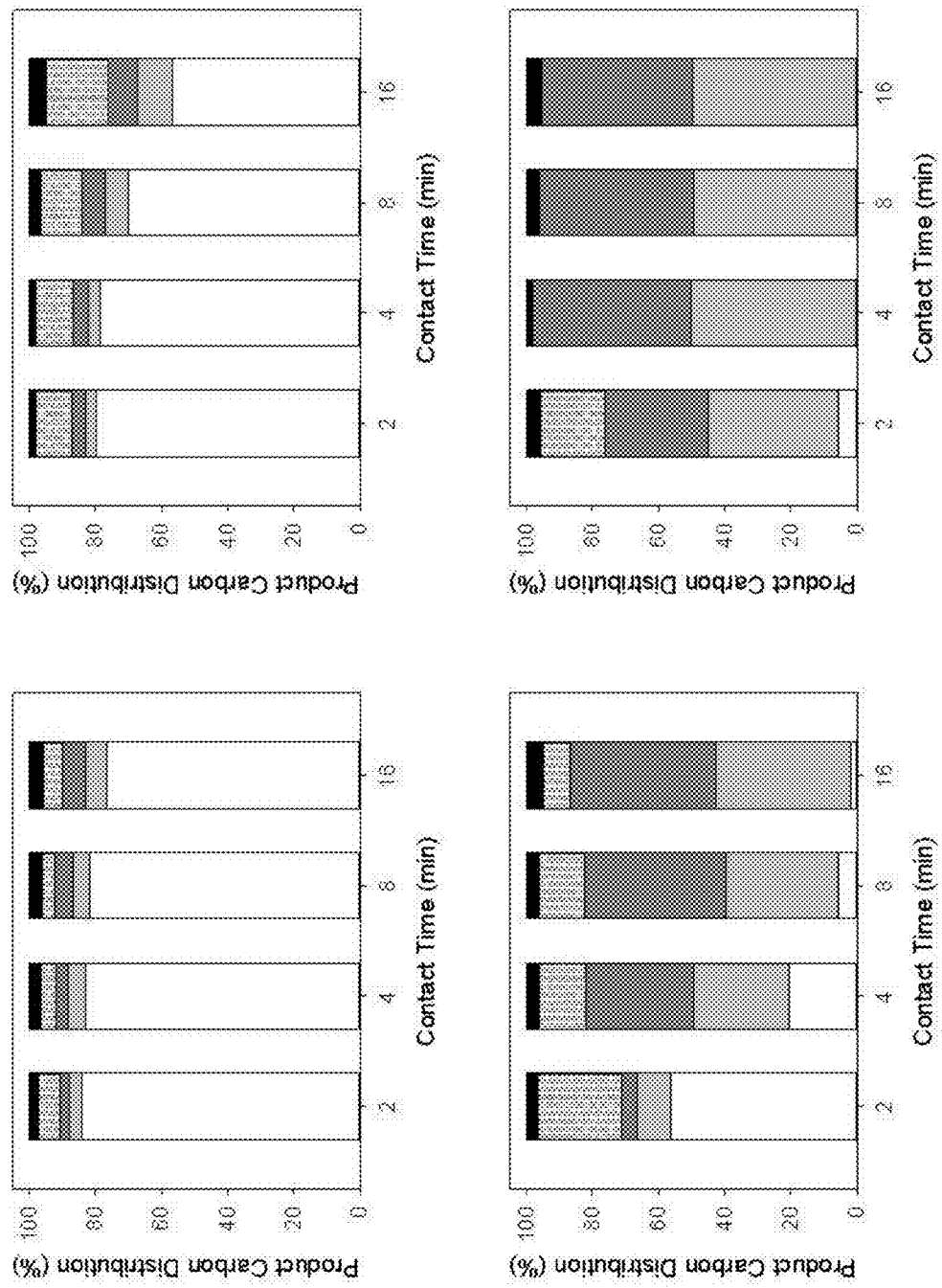
FIG. 5 is a series of graphs showing the summary of carbon distributions in analyzed products as a function of contact time at four temperatures (523 K, 548 K, 573 K, and 598 K, where various products are represented as follows: (white fill)

Referring to FIG. 5, the carbon distribution obtained during LA oxidation over VOx/Al2O3 at the conditions reported in FIG. 6 was measured. Carbon distributions in analyzed products were determined as a function of contact time. For each experiment summarized, carbon balances closed to above 90%, and the illustrated carbon distributions reflect quantified reaction products. At lower contact times, several species other than MA and LA were identified and monitored. α-angelica lactone (AAL) was present as the dehydration product of pseudo-levulinic acid. AAL can isomerize to β-angelica lactone (BAL), traces of which were present. Methyl vinyl ketone (MVK) was identified in small quantities, either as a result of direct decarbonylation of levulinic acid, or as a result of decarbonylation of AA1 and BAL. 4-cyclopentene-1,3-dione (DIO) was the last species to be identified at appreciable amounts.

FIG. 5 relates the selectivities of all species to their contact time on $VO_x$/$Al_2O_3$ at 573° K. Carbon oxides ($CO_x$) become increasingly prevalent under more severe conditions of high temperature and contact time. It is worth noting that angelicalactone formation is reversible such that, as LA is consumed by oxidative cleavage, angelicalactones should also be converted to cleavage products via reversible LA formation. Formation of MA via cleavage of the C5 carbon in LA is anticipated to produce a stoichiometric equivalent of formaldehyde or formic acid, which one would expect will decompose to COx under these conditions; however, this is not sufficient to explain the roughly equivalent quantities of carbon recovered as MA and COx. Most likely, COx formation results from parallel cleavage pathways that form intermediates, such as acetic or maloic acid, which might further decompose to carbon oxides. Dione selectivity appears to peak at moderate temperatures and contact times, while at high temperatures, the dione formation is minimal. Operating at 350° C. or above appears to enhance MA selectivity at the expense of the dione, which could be attributed to the oxidation being a higher barrier process and at sufficiently high temperatures, LA is consumed by oxidation more rapidly than dione formation.

The role of $O_2$ partial pressure was tested on a $VO_x/Al_2O_3$ catalyst by holding the temperature, LA partial pressure and WHSV constant, while testing an array of $O_2$ lean to $O_2$ rich environments. The results are presented in Table 2 and FIG. 6. Experiments here carried out at 623 K, pLA=0.0158 bar, WHSV=0.128 min$^{-1}$. Carbon balance closure for each data point was within 5%. Even under oxygen deficient conditions, baseline conversion of LA is observed. Under these conditions, product selectivity is primarily toward angelicalactones, which is an acid catalyzed transformation and should occur under anaerobic conditions. As the $O_2$ pressure increases, a pronounced shift in selectivity was observed toward MA/COx, and MA formation appears to occur at the expense of angelicalactones. Most likely, the rate of angelicalactone formation remains rapid relative to oxidative cleavage under all conditions; however, the reaction is reversible such that as LA is consumed by irreversible oxidation, angelicalactones will form LA such that angelicalactone formation does not limit MA yields; rather, under sufficiently oxidizing conditions or long contact times, all LA and AL can, in theory, be converted to MA.

As shown in FIG. 6, the selectivity toward MA increases linearly with oxygen partial pressure, indicating that the oxidative cleavage of LA to form MA is higher order in $O_2$ than competing side reactions. This stands to reason as angelicalactones and diones both most likely form through non-oxidative pathways and we would expect their rates to be independent of $O_2$ partial pressure. Since side reactions are likely zero order in oxygen, this result suggests that the oxidative cleavage of LA to form MA is first order in $O_2$ partial pressure under the conditions tested. Table 2 below shows the results for the $O_2$ partial pressure experiments with the partial pressure of the organic feed is 0.016 bar, the temperature fixed at 573° K, and WHSV is fixed at 0.13 min$^{-1}$.

TABLE 2

| Entry | Feed | LA:$O_2$ | Conversion (%) | MA yield[a] (%) | $C_4$ Selectivity (%) | $C_2$ Selectivity (%) |
|---|---|---|---|---|---|---|
| 1 | LA | 0.019 | 100 | 55.3 | 55.3 | 4.0 |
| 2 | LA | 0.024 | 100 | 43.6 | 43.7 | 4.4 |
| 3 | LA | 0.048 | 93 | 19.9 | 21.3 | 3.6 |
| 4 | LA | 0.096 | 81 | 9.1 | 11.2 | 2.9 |
| 5 | LA | 0.193 | 71 | 4.0 | 5.6 | 1.7 |
| 6 | LA | 1.608 | 42 | 0.5 | 1.2 | 0.9 |

A significant portion of selectivity losses appears to be non-oxidative in nature (e.g., angelicalactone formation, dione formation) and may be associated with other catalyst functionalities (e.g., acid/base). Moreover, the structure and activity of supported vanadates is well-documented to vary significantly with the identity of the support. Accordingly, a comparison of the performance of VOx on multiple supports to that of bulk $V_2O_5$ was performed to identify those materials that offer enhanced activity and/or selectivity to oxidative cleavage and MA formation. Results are summarized in Table 3 below, which shows a summary of LA oxidation over both unsupported $V_2O_5$ and VOx supported on $Al_2O_3$, $SiO_2$, $TiO_2$

TABLE 3

| Entry | Catalyst | T (K.) | Contact Time (min) | LA Conv. (%) 548 K. | MA Yield (%) | Carbon Selectivity (%) | | | | | MA/ Cox |
|---|---|---|---|---|---|---|---|---|---|---|---|
| | | | | | | Ang | Mac | Cox | Dione | Other | |
| 1 | VOx/ $Al_2O_3$ | 548 | 1.95 | 31 | 1 | 80 | 3 | 4 | 11 | 2 | 0.7 |
| 2 | VOx/ $SiO_2$ | 548 | 1.95 | 99 | 50 | 2 | 43 | 36 | 15 | 5 | 1.2 |
| 3 | VOx/ $TiO_2$ | 548 | 1.56 | 93 | 21 | 14 | 28 | 38 | 14 | 6 | 0.7 |
| 4 | VOx/ $Al_2O_3$ | 548 | 78.0 | 99 | 34 | 3 | 28 | 36 | 24 | 9 | 0.8 |
| 5 | $V_2O_5$ | 548 | 280 | 97 | 18 | 12 | 15 | 21 | 45 | 6 | 0.7 |
| 6 | VOx/ $SiO_2$ | 523 | 3.90 | 37 | 1 | 83 | 2 | 5 | 8 | 2 | 0.49 |
| 7 | VOx/ $SiO_2$ | 548 | 3.90 | 100 | 48 | 1 | 44 | 35 | 14 | 6 | 1.27 |
| 8 | VOx/ $SiO_2$ | 573 | 3.90 | 100 | 71 | 0 | 57 | 37 | 2 | 5 | 1.55 |

As summarized in FIG. 3, optimal MA yields of roughly 55-60% over VOx/g-$Al_2O_3$ was observed at 598° K with the predominant loss of selectivity attributed from COx formation. Since the ratio of COx to MA generally exceeds unity, it suggests that COx species are arising from competing cleavage and decomposition pathways. Accordingly, it may be possible to improve MA yields by designing a catalyst that is more selective toward terminal C—C cleavage and minimizes alternate pathways. One strategy to improve selectivity may be to work at lower temperatures where overoxidation might be controlled; however, we observe a significant quantity of dione formation under these conditions. It has been well-established that the activity of supported vanadates scales with the nature of the support. Further, LA has multiple functionalities and can react via acid/base catalyzed pathways in parallel to oxidative pathways. Likely, some of the above reported selectivity losses are associated with support functionality since γ-$Al_2O_3$ is relatively acidic. As such, it may be possible that employing inert supports could minimize side reactions and additionally help to improve MA yields. Accordingly, the activity of VOx supported on γ-$Al_2O_3$ was compared to analogous systems of VOx/$SiO_2$, VOx/$TiO_2$, and $V_2O_5$. Comparing all supports at 548 K (Table 2), VOx/$SiO_2$ and VOx/$TiO_2$ was observed to be significantly more active than VOx/$Al_2O_3$, achieving complete LA conversion at substantially lower contact times. Bulk $V_2O_5$ was the least reactive and did not achieve complete LA conversion until a contact time of roughly 300 minutes. Comparing each sample at complete LA conversion (entries 2-5), VOx/$Al_2O_3$, VOx/$TiO_2$ and $V_2O_5$ give comparable MA selectivities on the order of 20-30%, whereas VOx/$SiO_2$ achieved an MA selectivity of 43%. Moreover, VOx/$SiO_2$ was the only catalyst that achieved an MA/COx ratio greater than unity suggesting the extent of overoxidation and/or parallel cleavage pathways is minimized on this catalyst. Based on its improved activity and MA selectivity relative to COx species, the performance of VOx/$SiO_2$ was explored further over a range of temperatures at a contact time of 3.9 min. In this experiment, MA selectivity increased dramatically with reaction temperature, and a MA (Carbon) selectivity of 57% and a MA/COx ratio of 1.55 at a temperature of 573° K was obtained. This corresponds to a MA yield of 71% of the theoretical maximum, and is the highest yield observed in this system to date. Based on this preliminary screening, it is evident that the nature of the support has a significant impact on both the activity and oxidation selectivity; however, it is difficult to identify the nature of this variation in the current study. The structure of VOx clusters varies considerable with support and loading, and it is not possible with the characterization presented here to distinguish between different vanadates in these materials. Subsequent studies will examine variation in oxidation rates and selectivity with site structure and should allow further optimization of MA yields.

What is claimed is:

1. A process for making maleic acid, its isomer fumaric acid, or maleic anhydride, from levulinic acid, comprising the steps of:
   vaporizing levulinic acid in the presence of an insert gas and an oxidizing gas at a first predetermined temperature and a predetermined pressure such that the levulinic acid partial pressure is below the vapor pressure of levulinic acid at the predetermined temperature to produce a feed stream;
   heating the feed stream to a second predetermined temperature without initiating polymerization to produce a thermally equilibrated gas stream; and
   oxidatively cleaving the gas stream to a third predetermined temperature in the presence of a catalyst.

2. The method of claim 1, wherein the first predetermined temperature is less than or equal to 150 degrees Celsius.

3. The method of claim 2, wherein the second predetermined temperature is between 200 and 500 degrees Celsius.

4. The method of claim 3, wherein the third predetermined temperature is above 523 degrees Kelvin.

5. The method of claim 4, wherein the step of oxidatively cleaving the gas stream comprising the step of passing the gas stream over a reducible oxide catalyst in a single packed bed reactor.

6. The method of claim 5, wherein the catalyst is VOx/$Al_2O_3$.

7. The method of claim 6, wherein the levulinic acid partial pressure is 0.0158 bar.

8. The method of claim 7, wherein the oxidizing gas is oxygen.

9. The method of claim 8, wherein the oxygen is provided at a mole fraction between 0 and 1.

* * * * *